(12) United States Patent
Tallhamer et al.

(10) Patent No.: US 10,441,818 B2
(45) Date of Patent: *Oct. 15, 2019

(54) PATIENT MONITORING SYSTEM

(71) Applicant: Vision RT Limited, London (GB)

(72) Inventors: Michael James Tallhamer, Aurora, CO (US); Adrian Roger William Barrett, London (GB); James Mathew Hughes, II, Columbia, MD (US); Edward William Mead, London (GB); Ivan Daniel Meir, London (GB)

(73) Assignee: VISION RT LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/698,034

(22) Filed: Sep. 7, 2017

(65) Prior Publication Data

US 2017/0368370 A1    Dec. 28, 2017

Related U.S. Application Data

(63) Continuation of application No. 15/098,094, filed on Apr. 13, 2016, now Pat. No. 9,789,338.

(51) Int. Cl.
*G06K 9/00* (2006.01)
*A61N 5/10* (2006.01)
*G06T 7/521* (2017.01)
*G06T 7/593* (2017.01)
*A61B 34/10* (2016.01)
(Continued)

(52) U.S. Cl.
CPC ............ *A61N 5/1049* (2013.01); *G06T 7/521* (2017.01); *G06T 7/593* (2017.01); *A61B 90/18* (2016.02); *A61B 2034/105* (2016.02); *A61B 2090/309* (2016.02); *A61B 2090/371* (2016.02);
(Continued)

(58) Field of Classification Search
CPC ..................... A61N 2005/1059; A61N 5/1049
See application file for complete search history.

(56) References Cited

U.S. PATENT DOCUMENTS 7,348,974 B2    3/2008   Smith et al.
7,889,906 B2    2/2011   Smith et al.
(Continued)

FOREIGN PATENT DOCUMENTS

WO     03061477 A1    7/2003
WO   2004032781 A1    4/2004

OTHER PUBLICATIONS

International Search Report and Written Opinion for PCT Patent App. No. PCT/GB2017/051003 (dated Jul. 7, 2017).

*Primary Examiner* — Oneal R Mistry
(74) *Attorney, Agent, or Firm* — Birch, Stewart, Kolasch & Birch, LLP (57) ABSTRACT

A patient monitoring system for monitoring a patient undergoing radiotherapy comprising a projector operable to project a pattern of light onto a patient undergoing radiation treatment, a patient restraint operable to restrain the patient relative to a treatment apparatus, an image detector operable to obtain images of the patient, and a model generation module operable to process images of the patient obtained by the image detector to generate a model of the surface of a portion of the patient, wherein at least a portion of the patient restraint is colored and the model generation module is inhibited from generating a model of the colored portion of the patient restraint.

17 Claims, 7 Drawing Sheets

(51) Int. Cl.
    *A61B 90/18*    (2016.01)
    *A61B 90/30*    (2016.01)
    *A61B 90/00*    (2016.01)

(52) U.S. Cl.
    CPC ............... *A61N 2005/1059* (2013.01); *A61N 2005/1097* (2013.01)

(56)            References Cited

U.S. PATENT DOCUMENTS

| | | |
|---|---|---|
| 8,135,201 B2 | 3/2012 | Smith et al. |
| 8,662,083 B2 | 3/2014 | Meir et al. |
| 2003/0136924 A1 | 7/2003 | Kraft et al. |
| 2004/0053237 A1* | 3/2004 | Liu ............... B01L 3/502707 506/9 |
| 2009/0316965 A1 | 12/2009 | Mailling et al. |
| 2011/0228907 A1* | 9/2011 | Gagnon ............... A61G 15/02 378/65 |
| 2015/0062303 A1 | 3/2015 | Hanson et al. |
| 2015/0265852 A1 | 9/2015 | Meir et al. |
| 2016/0000516 A1* | 1/2016 | Cheng ............... A61B 34/20 600/424 |
| 2016/0090479 A1* | 3/2016 | Takahashi ............ G02B 5/3083 524/523 |
| 2016/0271421 A1* | 9/2016 | Nieberding ............ A61B 90/18 |

* cited by examiner

PATENT MONITORING SYSTEM

CROSS REFERENCE TO RELATED APPLICATION

This application is a continuation of U.S. patent application Ser. No. 15/098,094 filed Apr. 13, 2016, the contents of which are hereby incorporated in its entirety by reference.

FIELD OF THE INVENTION

The present invention relates to a patient monitoring system, in particular to a patient monitoring system including a patient restraint for immobilizing a patient during treatment.

BACKGROUND TO THE INVENTION

Radiotherapy consists of projecting onto a predetermined region of a patient's body, a radiation beam so as to eliminate or reduce malignant or benign tumors existing therein as well as treating non-cancerous ailments. Such treatment is usually carried out periodically and repeatedly. At each medical intervention, the patient must be positioned with respect to the radiation source in order to irradiate the selected region with the highest possible accuracy to avoid radiating adjacent tissue on which radiation beams would be harmful. If movement of a patient is detected during treatment, the treatment should be halted to avoid irradiating areas of a patient other than the treatment location.

For this reason a number of monitoring systems for assisting the positioning of patients during radiotherapy and detecting patient movement have therefore been proposed such as those described in Vision RT's earlier patents and patent applications U.S. Pat. Nos. 7,889,906, 7,348,974, 8,135,201, US2015/062303 and US2015/0265852.

In the systems described in Vision RT's patent applications, images of a patient are obtained using a stereoscopic camera of a speckled pattern projected onto a portion of the patient being monitored. A model generation module determines transformations to identify and match corresponding portions of these images received by the left and right lenses of the stereoscopic camera. These matches are then utilized to generate a 3D model of the patient which is compared with a stored reference model of the surface of the patient when correctly positioned to confirm the patient is in the correct position. Typically such a comparison involves undertaking Procrustes analysis to determine a transformation which minimizes the differences in position between points on the surface of a patient identified by data generated based on live images and points on the stored reference model of the surface of a patient.

For stereotactic surgery, in particular when treating brain tumors, it is essential that the patient is positioned relative to the radiation delivery system with very high accuracy so that radiation is delivered to the tumor, and not the surrounding healthy tissue. For this reason, the head of a patient undergoing stereotactic surgery is securely attached to a couch via a patient restraint such as a head mask so that the patient cannot move their head during treatment. The same considerations apply in the case of other types and locations of tumor where alternative patient restraints are employed.

A patient restraint such as a mask is normally made out of a thermoplastic material which is heated prior to an initial treatment session. The mask is then molded to a patient's head by being placed over the patient's face and then allowed to set. The resultant head mask completely encloses a patient's head and thus restricts movement and allows a patient to be placed into a fixed position for each treatment session. Examples of such full head masks are disclosed in WO03/061477 and WO04/032781. Although a full-head mask is an improvement on immobilizing a patient solely with a chin strap, as the mask completely obscures a patient's face, it is not possible to monitor for movement of the face during treatment. This problem has been addressed by using an alternative head mask described U.S. Pat. No. 8,662,083 which includes an aperture arranged to leave a patient's face substantially free to allow for monitoring by a stereoscopic camera.

Improvements in patient monitoring systems are still desired.

SUMMARY OF THE INVENTION

According to one aspect of the present invention there is provided a patient monitoring system comprising: a projector operable to project a pattern of light onto a patient undergoing treatment, a patient restraint operable to restrain the patient relative to a treatment apparatus, and a stereoscopic camera operable to obtain stereoscopic images of the patient and the patient restraint. A model generation module is then provided which is operable to process stereoscopic images obtained by the stereoscopic camera to generate a model of the surface of a portion of a patient appearing in the images onto which the pattern of light is projected. At least a portion of the patient restraint is colored and the model generation module is inhibited from generating a model of the colored portion of the patient restraint.

In some embodiments the model generation module is arranged to process stereoscopic images to identify portions of images corresponding to the colored portion of a patient restraint and only to attempt to identify corresponding portions of stereoscopic images outside the identified areas of the images.

Preferably, the colored portion of the patient restraint is arranged to absorb a substantial proportion of the projected light projected by the projector so that the projected pattern is not readily apparent in the portion of the images corresponding to the restraint. This reduces the ability of the modeling system to match portions of images corresponding to the patient restraint. Where matches occur they are much more likely to correspond to the surface of the patient and hence the accuracy of the system is improved.

This may be achieved by the color of the restraint being substantially black so as to absorb a substantial proportion of the projected light. In other embodiments the color of the patient restraint may be selected so as to correspond to a color associated with the wavelength of the projected light so that the projection of the patterned light onto the surface of the restraint is not readily apparent and hence the modelling system does not identify matches in portions of images corresponding to the surface of the restraint. In some embodiments the restraint may be colored black.

In some embodiments the coloring of a restraint may be achieved by the inclusion of a suitable dye within the thermoplastic from which a restraint is formed. Alternatively, a suitable coloring may be applied to the exterior of the restraint after the restraint has been molded.

Preferably the restraint is selected to have low reflectivity so as to reduce the incidents of specular highlights appearing in images of the restraint and the structure of the restraint is selected so that holes and perforations appearing in images of the restraint obtained by a patient monitor are of a different size to portions of a pattern of light projected onto the restraint utilized by the modelling system to identify corresponding portions of stereoscopic images.

According to another aspect of the present invention there is provided a patient monitoring system comprising: a patient restraint operable to restrain the patient relative to a treatment apparatus, wherein at least a portion of the patient restraint is colored; a camera system operable to obtain stereoscopic and further images of a portion of the patient being monitored; and a model generation module operable to process stereoscopic images obtained by the stereoscopic camera to generate a model of the surface of a portion of a patient appearing in the images and to process the further images to texture render the generated model of the portion of the patient; wherein the patient monitoring system is configured to monitor the position of a patient on the basis of the portion of the generated model which is not texture rendered a color corresponding to the color of the patient restraint.

The monitoring system may be operable to compare the portion of the generated model which is not texture rendered a color corresponding to the color of the patient restraint with a stored model of the surface of a patient and to generate positioning instructions to match the portion for the generated model with the stored model.

In some embodiments the colored portion of the patient restraint may be patterned and the patient monitoring system may be configured to identify portions of a generated model texture rendered with the pattern corresponding to the pattern appearing on the colored portion of the patient restraint.

In some embodiments the colored portion of the patient restraint may be a border around an aperture in the restraint and the patient monitoring system may be configured to monitor the position of a patient on the basis of the portion of the generated model which is contained within the section of a model texture rendered a color corresponding to the colored border.

BRIEF DESCRIPTION OF THE DRAWINGS

The invention will now be described by way of example only with reference to the accompany drawings, in which.

DETAILED DESCRIPTION OF THE PREFERRED EMBODIMENTS

Figure 1:
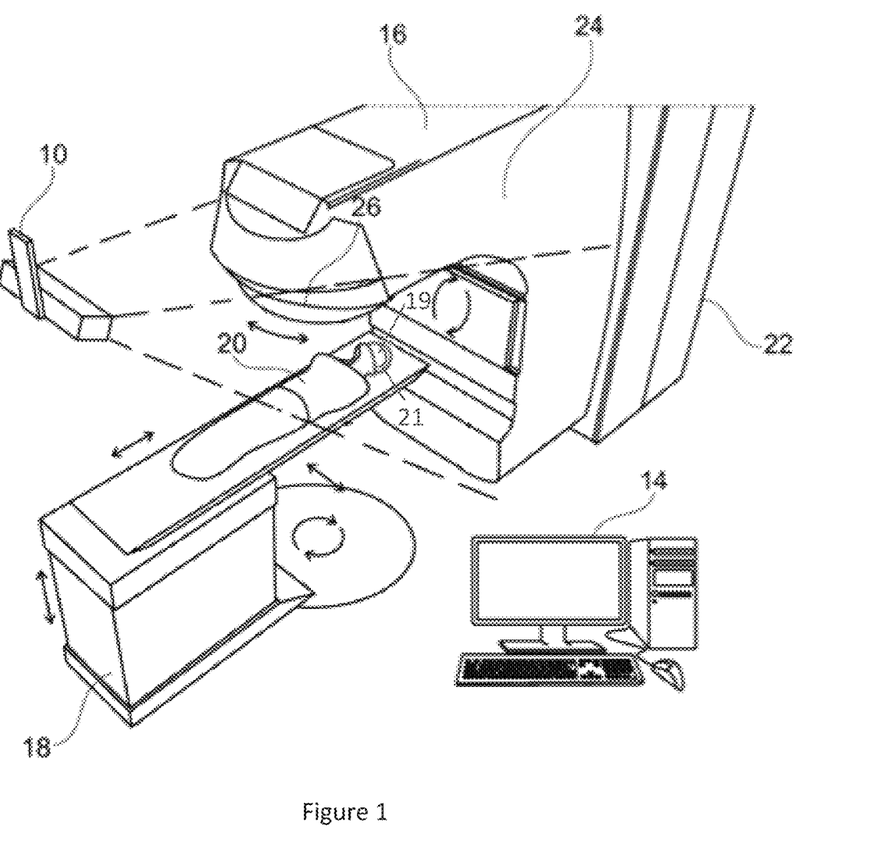
FIG. 1 is a schematic perspective view of a patient monitoring system in accordance with an embodiment of the present invention.

The patient monitoring system comprises a stereoscopic camera system 10 that is connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the center of the main body 22 of the treatment apparatus 16. Additionally the location of irradiation by the treatment apparatus may also be varied by rotating the collimator 26 at the end of the gantry 24.

In this embodiment a patient restraint in the form of a head mask 21 is used to restrain the head 19 of the patient 20 undergoing treatment.

In use, the stereoscopic camera 10 obtains video images of the patient 20 lying on the mechanical couch 18. These video images are passed via the wiring to the computer 14. The computer 14 then processes the images of the patient 20 to generate a model of the surface of the patient being treated. In this embodiment which concerns stereotactic brain surgery, the model of the surface of the patient will comprise a model of the surface of a portion of the patient's head and face.

This model can be compared with a model of the patient generated during earlier treatment sessions. When positioning a patient the difference between a current model surface and a target model surface obtained from an earlier session is identified and the positioning instructions necessary to align the surfaces are determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

As will be explained in greater detail, in order to enable the computer 14 to generate a model of the surface of a patient 20, a random pattern of light is projected onto the surface of the patient 20. This assists the computer 14 when identifying corresponding portions of stereoscopic images of the patient 20.

In this embodiment, the head mask 21 is colored so that the projected pattern of light onto the head mask 21 is not readily apparent in images obtained by the stereoscopic camera 10. This can be achieved by coloring the head mask 21 a matt black color so that the projected light is substantially absorbed by the head mask 21. Alternatively the color of the mask 21 could be selected to be substantially similar to the color of the projected light.

Coloring the head mask 21 in this way inhibits the matching algorithm from identifying matches in the portions of the stereoscopic images corresponding to the head mask 21. As a result the model generated by the computer 14 avoids incorporating portions of the surface of the head mask 21 into the model. This improves the accuracy with which a patient can be positioned since the match between the generated model and a previously stored model corresponds only to the surface of the patient 20.

Figure 2:
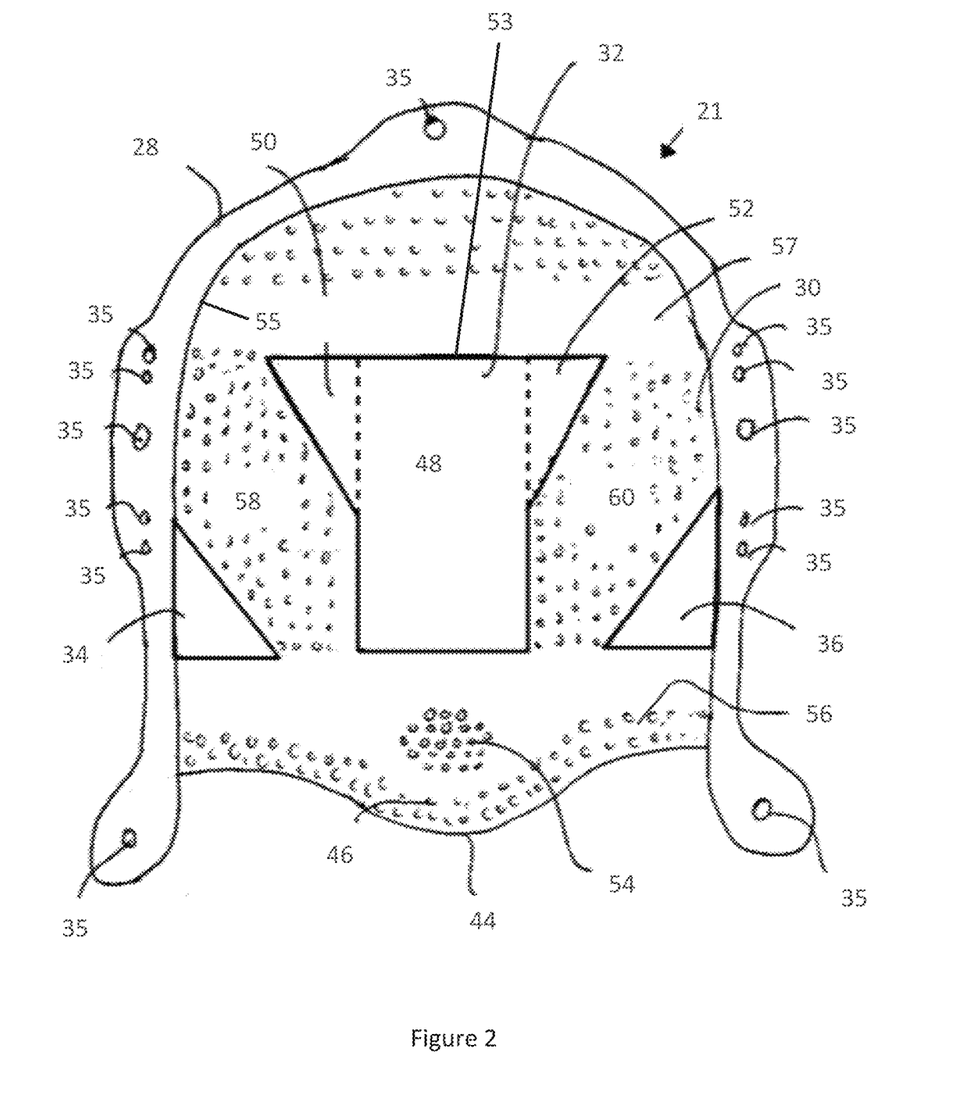
FIG. 2 is a frontal view of a blank for a head mask of the patient monitoring system of FIG. 1.
Figure 3:
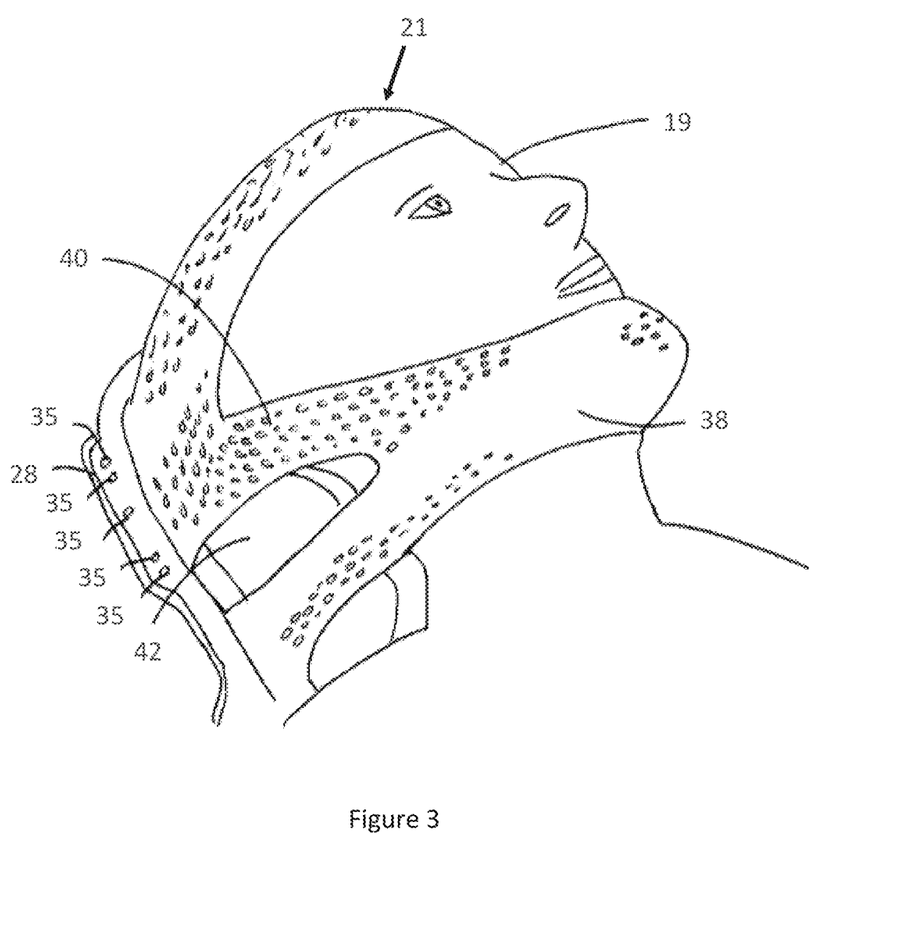
FIG. 3 is a perspective view of the head and neck of a patient wearing a head mask formed from the blank of FIG. 2.

FIG. 2 is a front view of a head restraint blank 21 in accordance with the present embodiment of the present invention. The blank 21 is also illustrated in FIG. 3 which comprises a schematic perspective view of the head restraint blank 21 after deformation by a patient's head 19.

The head mask 21 comprises a rigid U-shaped frame 28 with an integrally formed perforated sheet 30. The perforated sheet 30 is made from a thermoplastic which when heated can be deformed by being placed over a patient's head.

In this embodiment the head mask 21 is made of any thermoplastic which is suitable for being deformed over the patient's head without causing discomfort, i.e. the thermoplastic must soften at a temperature low enough so the patient's skin is not burnt. Suitable thermoplastics that melt or soften at temperatures ranging from 50° C. to 100° C. include poly (ethyleneadipate), poly (epsilon-caprolactone), polyvinyl stearate, cellulose acetate, butyrate and ethyl cellulose poly (propylene oxide) containing comonomers, trans polyisoprene and cis polyisoprene based thermoplastic materials, and polycaprolactone based materials.

In this embodiment the head mask 21 is colored black so as to absorb a significant proportion of patterned light projected onto its surface such that the patterned light is not readily discernible in obtained images of the head mask 21. The head mask 21 can be colored during the molding of the thermoplastic using a suitable pigment, or post-molding using a coating. Suitable coatings will include deep-black chalkboard paint such as is used to blacken the interiors of optical telescopes to minimize stray light in the light path. If a coating is used the coating should preferably be hypoallergenic so as to minimize the risk of reaction with a patient's skin.

In this embodiment the perforated sheet 30 has three large apertures comprising a main central aperture 32 and two subsidiary triangular apertures 34,36 provided either side of the main central aperture 32. A series of screw holes 35 are provided in the frame 28 enabling the frame 28 to be attached to a restraint platform.

In FIG. 3, the arrangement of the apertures 32,34,36 in the perforated sheet 30 is such that when the head mask 21 is deformed by being placed over the patient's face, the perforated sheet 30 is molded and stretched to sculpt the contours of the patient's head 19 whilst leaving the patient's face, including eyes, nose and mouth, to be uncovered. At the same time the portions of the perforated sheet 30 between the apertures 32,34,36 are stretched so as to form a chin strap 38 and a pair of accompanying side struts 40 either side of the patient's face which together act to restrain the patient's head 19 in place whilst giving the deformed sheet 30 substantial structural rigidity thus ensuring that despite the fact that the patient's face is unenclosed, the mask acts to retain the patient's head 19 in a fixed position when it lies on a cushion 42 provided as part of a restraint platform. In addition to being more comfortable for a patient, leaving the patient's face uncovered enables movement of the patient to be detected using non-contact motion detection systems such as Vision RT's AlignRT® system such as is disclosed in U.S. Pat. No. 7,889,906.

In FIG. 2, before being deformed the perforated sheet 30 substantially fills the entirety of the U-shaped frame 28 with the edge 44 of the perforated sheet 30 at the open end of the U-shaped frame 28 following a serpentine curve initially running approximately perpendicularly to the arms of the frame 28 before moving away from the apex of the U-shaped frame 28 so as to provide a small additional protrusion 46 in the central portion of the sheet 30. As is shown in FIG. 2 this protrusion 46 is such to enable the portion of the perforated sheet 30 to form a chin strap 38 which encloses a patient's chin when the head mask 21 has been deformed.

In this embodiment, the main central aperture 32 comprises a central rectangular portion 48 and two adjacent wing portions 50,52 where, the central rectangular portion 48 extends across the middle third of the perforated sheet 30 with the longer sides of the central rectangular portion 48 running parallel with the arms of the U-shaped frame 28. The two wing portions 50,52 each comprise right angled triangular openings each with bases extending half way down the long sides of the central rectangular portion 48 and with each wing portion 50,52 having an apex level with the edge 53 of the central rectangular portion 48 remote from the edge 44 of the perforated sheet 30 half way between the long side of the central rectangular portion 48 and the edge 55 of the U-shape frame 28.

In this embodiment, in order to increase the resistance of some areas of the perforated sheet 30 to deformation, some areas of the sheet 30 are left free of perforations. More specifically, other than in a central area 54 of the section of the sheet 30 and a band 56 immediately adjacent to the open end of the U-shaped frame 28, the portion of the sheet 30 adjacent to the open end of the U-shaped frame 28 is left free from perforations. In use this causes the central area 54 and the section of sheet 30 immediately adjacent to the open end of the U-shaped frame 28 to deform more easily and so accommodate the shape of a patient's chin. Also a band 57 of sheet 30 running across the edge of the main aperture 32 remote from the open end of the U-shaped frame 30 extending across to the arms of the frame 28 is also left free from perforations.

The two subsidiary triangular apertures 34,36 each comprise a right-angled triangular opening. The two subsidiary triangular apertures 34,36 lie either side of the main central aperture 32 with a base adjacent to the arms of the U-shaped frame 28 and apex level with the end of the edge of the central rectangular portion 48 of the main central aperture 32 with the hypotenuses of the winged portions 50,52 of the main aperture 32 and the triangular apertures 34,36 being parallel to each other.

In this way, the edges of main aperture 32 and the two subsidiary triangular apertures 34,36 define the edges of a pair of strips 58,60 of the perforated sheet 30 lying either side of the main aperture 32 connecting the U-shaped frame 28 with the portion of the sheet 30 adjacent to the open end of the U-shaped frame 28. In use as is shown in FIG. 3, these strips 58,60 are deformed so as to form the struts 40 connecting the chin strap 38 formed from the portion of the sheet 30 adjacent to the open end of the U-shaped frame 28 with a portion of the U-shaped frame 28 further from the open end of the frame 28.

Once set, after being deformed, the perforated sheet 30 will resist further deformation when placed under tension. In use the lower portion of the deformed sheet 30 acts to retain a patient's head 19 in position as this portion of the sheet 30 forms a chin strap 38 which prevents movement of a patient's chin away from the plane of the U-shaped frame 28. Similarly, the portion of the perforated sheet 30 remote from the open end of the U-shaped frame 28 prevents the forehead of a patient 20 from being moved away the plane of the U-shaped frame 28. Finally, the portion of the perforated sheet 30 remote from the open end of the U-shaped frame 28 and the struts 40 formed from the strips 58,60 between the main central aperture 32 and the two subsidiary apertures 34,36 together prevent movement the direction parallel with the arms of the U-shaped frame 28.

In particular, it will be noted that by providing the two subsidiary apertures 34,36 and the main central aperture 32 in the manner described above movement a head restraint is formed which resists motion but which has an opening which leaves a patient's face uncovered is formed. This is because the orientation of the struts 40 formed from the strips 58,60 between the main central aperture 32 and the two subsidiary apertures 34,36 are such to be placed under tension by any movement towards the open end of the U-shaped frame 28 and thus provide the head restraint with structural rigidity under tension even in the absence of the perforated sheet 30 covering the face of the patient.

Figure 4:
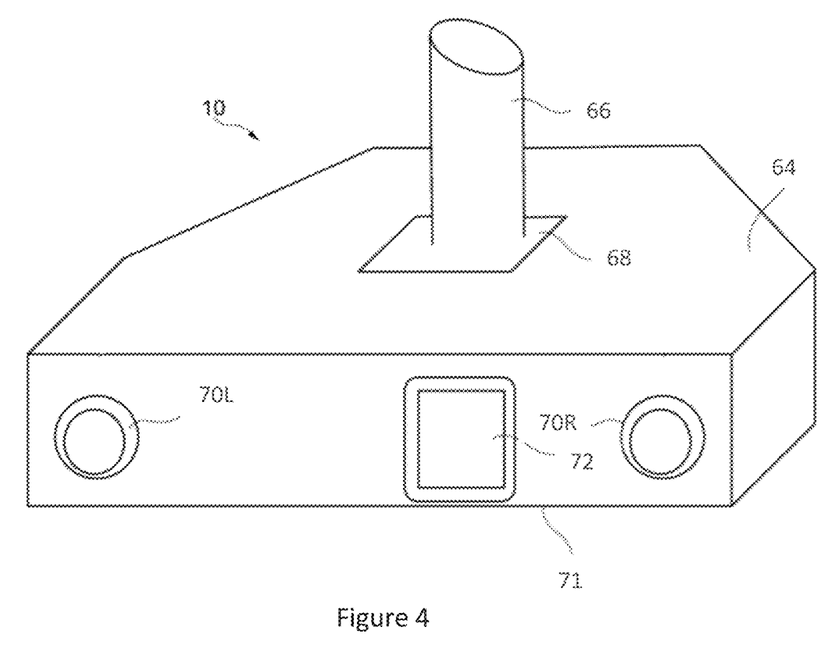
FIG. 4 is a front perspective view of the stereoscopic camera system of the patient monitoring system of FIG. 1.

FIG. 4 is a front perspective view of a stereoscopic camera system 10 of the patient monitoring system of FIG. 1.

In this embodiment the stereoscopic camera system 10 comprises a housing 64 which is connected to a bracket 66 via a hinge 68. The bracket 66 enables the stereoscopic camera system 10 to be attached in a fixed location to the ceiling of a treatment room whilst the hinge 68 permits the orientation of the stereoscopic camera system 10 to be orientated relative to the bracket 66 so that the stereoscopic camera system 10 is arranged to view a patient 20 on a mechanical couch 18.

A pair of lenses 70L,70R is mounted at either end of the front surface 71 of the housing 64. These lenses 70L,70R are positioned in front of image detectors such as CMOS active pixel sensors or charge coupled devices (not shown) contained within the housing 64. The image detectors are arranged behind the lenses 70L,70R so as to capture images of a patient 20 via the lenses 70L,70R. In some embodiments the housing 64 may be made of a material such as lead which provides very good shielding from radiation and thereby reduce the extent to which energetic particles generate random errors in images obtained by the image detectors.

A speckle projector 72 is provided in the middle of the front surface 71 of the housing 64 between the two lenses 70L,70R. The speckle projector 72 is arranged to illuminate a patient 20 with a pseudo random speckled pattern of infrared light so that when images of a patient 20 are captured by the two image detectors corresponding portions of captured images can be distinguished. To that end the speckle projector comprises a light source such as a LED and a film with a random speckle pattern printed on the film. In use light from the light source is projected via the film and as a result a pattern consisting of light and dark areas is projected onto the surface of a patient 20. When images of the projected speckle pattern are captured by the stereoscopic camera system 10 the images can then be processed to determine the positions of a set of points on the surface of the patient and hence the positioning of the patient can be monitored.

Figure 5:
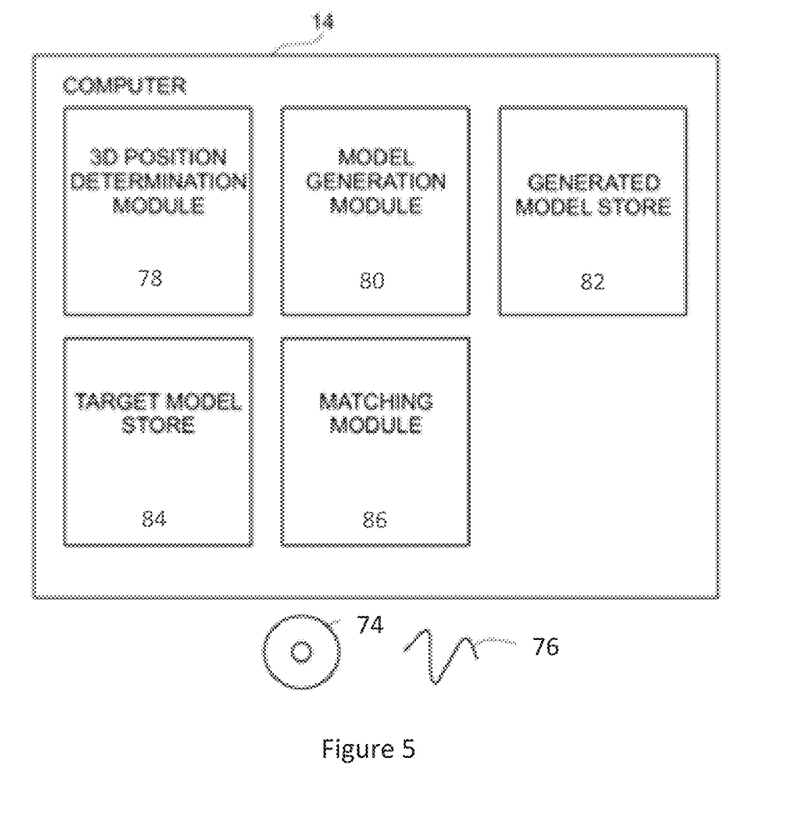
FIG. 5 is a schematic block diagram of the computer system of the patient monitoring system of FIG. 1.

FIG. 5 is a schematic block diagram of the computer 14 of the patient monitor of FIG. 1.

In order for the computer 14 to process images received from the stereoscopic camera system 10, the computer 14 is configured by software either provided on a disc 74 or by receiving an electrical signal 76 via a communications network into a number of functional modules 78-86. It will be appreciated that the functional modules 78-86 illustrated in FIG. 5 are purely notional in order to assist with the understanding of the working of the claimed invention and may not in certain embodiments directly correspond with blocks of code in the source code for the software. In other embodiments the functions performed by the illustrated functional modules 78-86 may be divided between different modules or may be performed by the re-use of the same modules for different functions.

In this embodiment, the functional modules 78-86 comprise: a 3D position determination module 78 for processing images received from the stereoscopic camera system 10, a model generation module 80 for processing data generated by the 3D position determination module 78 and converting the data into a 3D wire mesh model of an imaged surface; a generated model store 82 for storing a 3D wire mesh model of an imaged surface; a target model store 84 for storing a previously generated 3D wire mesh model; and a matching module 86 for determining rotations and translations required to match a generated model with a target model;

In use, as images are obtained by the stereoscopic camera system 10, these images are processed by the 3D position determination module 78. This processing enables the 3D position determination module 78 to identify 3D positions of points on the surface of a patient 20. This is achieved by the 3D position determination module 78 identifying corresponding points in pairs of images obtained by the lenses 70L,70R of the stereoscopic camera system 10 and then determining 3D positions for those points based on the relative positions of corresponding points in obtained pairs of images and stored data identifying the relative positions of cameras obtaining the images.

Typically the identification of corresponding points is based on analysis of image patches of around 16×16 pixels. In order to assist with identifying and matching corresponding patches as has been described the stereoscopic camera system 10 includes a speckle projector 72 arranged to project a pseudo-random speckle pattern onto the patient 20 being imaged so that different portions of the surface of the patient 20 can be more easily distinguished. The size of the speckle pattern is selected so that different patterns will be apparent in different image patches.

Figure 6:
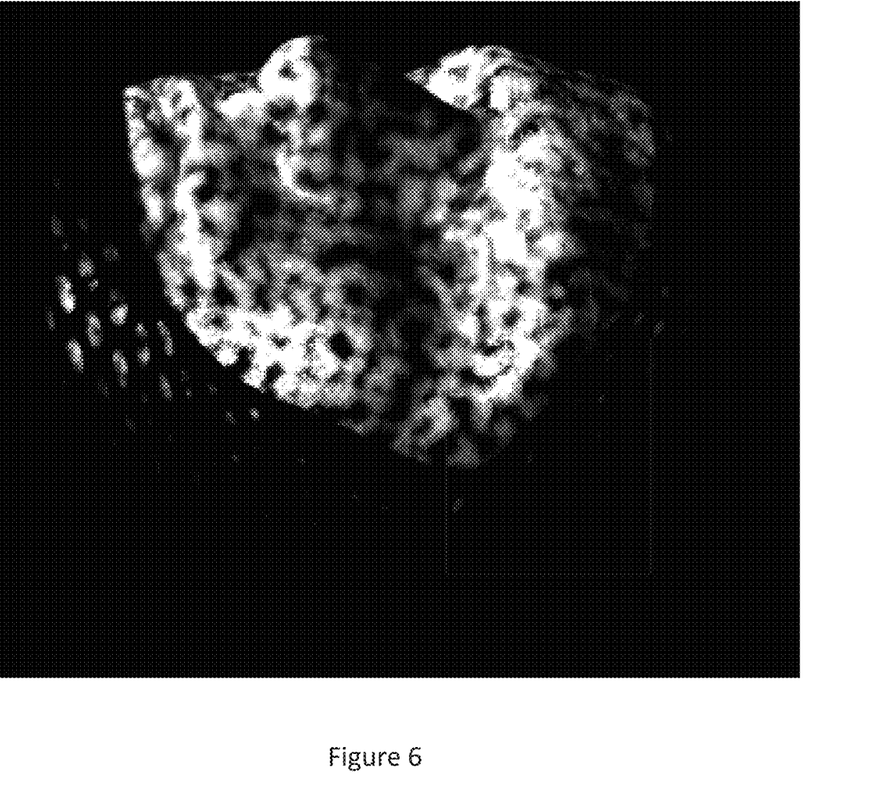
FIG. 6 is an illustrative example of an image captured by the patient monitoring system of FIG. 1.

FIG. 6 is an illustrative example of an image captured by the stereoscopic camera system 10 of the head of mannequin enclosed by a head mask 21 onto which a speckle pattern is projected. As can be seen in FIG. 6, the speckle pattern is visible in the portions of the image corresponding to the face of the mannequin. However, in the areas of the image corresponding to the head mask 21 which in this illustrative example has been painted with matt black paint the speckle pattern is not visible.

The position data generated by the 3D position determination module 78 is then passed to the model generation module 80 which processes the position data to generate a 3D wire mesh model of the surface of a patient 20 imaged by the stereoscopic cameras 10. As the speckle pattern is not readily detectable in the areas corresponding to the surface of the head mask 21, the 3D position determination module 78 is less likely to be able to identify corresponding portions in the stereoscopic images obtained by the stereoscopic camera 10 for these regions of the image and hence these areas are less likely to be included in a 3D wire mesh model generated by the model generation module 80.

In this embodiment the 3D model comprises a triangulated wire mesh model where the vertices of the model correspond to the 3D positions determined by the 3D position determination module 78. When such a model has been determined it is stored in the generated model store 82.

Figure 7:
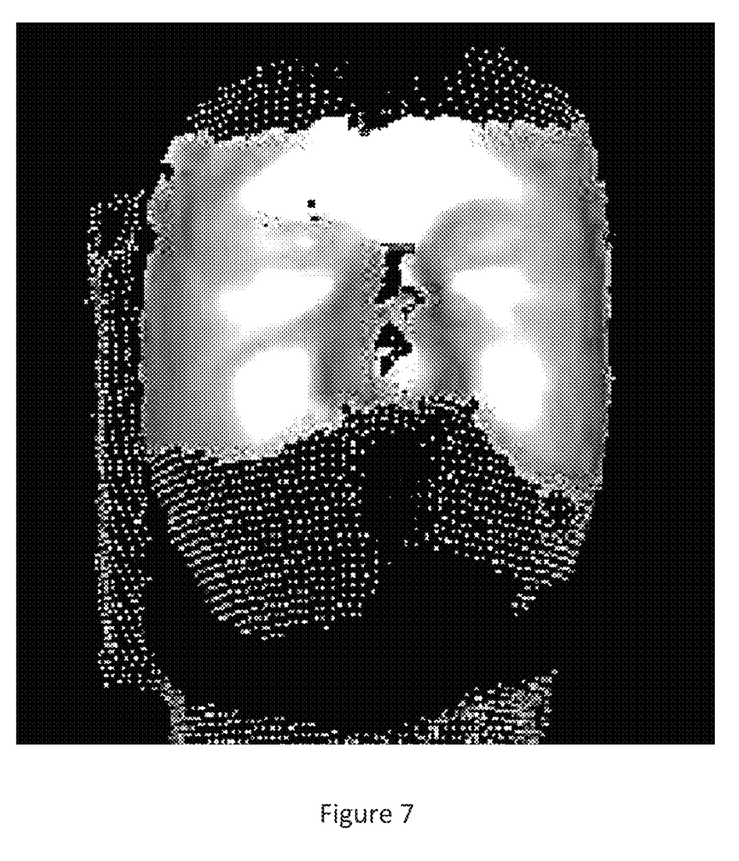
FIG. 7 is an illustrative example of a model surface generated by the patient monitoring system of FIG. 1.

FIG. 7 is an illustrative example of a 3D position data and a generated wire 3D wire mesh model corresponding to a front view of the mannequin shown in FIG. 6. In the exemplary illustration, individual 3D position points are shown as individual dots whereas in the central portion of the image where the density of 3D position data exceeds a threshold, the model is shown as a continuous surface.

As will be apparent from FIG. 7, although in the illustrated image matched data points are shown which correspond to the entirety of the head of the mannequin, the central portion of the image where the density of matches is greatest and for which a 3D wire mesh surface has been generated corresponds to points on the surface of the mannequin rather than points corresponding to points on the surface of the head mask 21.

When a wire mesh model of the surface of a patient 20 has been stored, the matching module 86 is then invoked to determine a matching translation and rotation between the generated model based on the current images being obtained by the stereoscopic cameras 10 and a previously generated model surface of the patient stored in the target model store 84. The determined translation and rotation can then be sent as instructions to the mechanical couch 18 to cause the couch to position the patient 20 in the same position relative to the treatment apparatus 16 as they were when they were previously treated. In the case of models generated utilizing a restraint such a colored head mask this will involve matching corresponding portions of a patient and hence the accuracy of the positioning of a patient will be improved as such matching will not be adversely impacted by any movement of the patient relative to the head mask 21 and any matching of points corresponding to the surface of the head mask 21 rather than the patient 20.

Subsequently, the stereoscopic cameras 10 can continue to monitor the patient 20 and any variation in position can be identified by generating further model surfaces and comparing those generated surfaces with the target model stored in the target model store 84. If it is determined that a patient has moved out of position, the treatment apparatus 16 can be halted and the patient 20 repositioned, thereby avoiding irradiating the wrong parts of the patient 20.

Although in the above embodiment, reference has been made to the head mask 21 being colored black, it will be appreciated that rather than being colored black, the head mask 21 could be of any color which absorbs light corresponding in color to the projected speckle pattern or otherwise reduces the visibility of the projected speckle pattern in images captured by the stereoscopic camera 10. Thus for example rather than being colored black a head mask 21 might be colored red so as to match the color of the speckle pattern projected onto the surface of patient.

It will also be appreciated that rather than only being concerned with thermoplastic head masks 21 for restraining a patient 20 during stereotactic brain surgery, the present invention also extends to and is equally applicable to other forms of restraint for use in relation any form of treatment such as radiotherapy or the like where high accuracy of patient positioning is required. Examples of such restraints will include full body restraints which mold to the shape of a patient to fix a patient relative to a positioning couch and other types of restraint which are molded to the surface of a patient and set so as to limit patient motion or to cause a patient to adopt a specified pose or orientation. In all such cases such restraints may be colored so as to reduce the generation of matches by a patient monitoring system.

Furthermore although in the above example a head mask 21 has been described which is colored black, it will also be appreciated that in other embodiments only a portion of the restraint might be colored.

Thus for example rather than coloring the entirety of the head mask 21 only the portion of the head mask 21 immediately adjacent the opening through which a patient's face is visible might be colored. In such a system matches in the colored area would be reduced and would serve to identify a boundary between portions of a model corresponding to a patient and matches corresponding to other matched points. Where such a boundary could be identified, the processing module could then be arranged to limit the generation of a 3D wire mesh model to points within the boundary.

In addition to coloring a restraint, other approaches can be made to reduce the matches being identified which correspond to a restraint rather than the surface of a patient being monitored.

Thus for example, preferably the surface of a restraint will be substantially dull and non-reflective so as to minimize specular highlights which might appear in images of the restraint which may be matched. Furthermore preferably a restraint will be designed so as to avoid having features of a size corresponding to the size of image patch used to identify corresponding features in stereoscopic image. Thus for example in the case of a restraint having holes or perforations, preferably the size of holes or perforations will be selected so as to be of a different size to the size of features matched in an image.

Although in the above embodiment a head mask is described in which the color of the head mask 21 is selected so as to impede the ability of a 3D position determination module 78 to identify corresponding portions of stereoscopic images, it will be appreciated that in some embodiments rather than selecting the color of all or part of a restraint to be such to absorb a speckle pattern the color of the restraint might be selected to be such to be easily detectable within images and the 3D position determination module 78 might be arranged to identify such sections of images and ignore such colored sections when attempting to identify matches.

In such an embodiment, the restraint, or a portion of the restraint adjacent the area of the patient being imaged, might be colored in an easily distinguishable color, for example, green. When the 3D position determination module attempts to identify corresponding portions of stereoscopic images, in contrast to the images of FIG. 6 where the speckle pattern is absorbed by the restraint and therefore only visible in the portions of the image corresponding to the face of the mannequin, the captured images will also include portions of the restraint which will be easily identifiable by the color or range of colors of the pixels making up the image corresponding to the specific identifiable color of the restraint. The 3D position determination module 78 could then be arranged so as not to process pixels of the identified color or range of colors corresponding to the head mask 21 when attempting to identify corresponding portions of stereoscopic images.

It will also be appreciated that in an alternative embodiment, a combination of image processing can take place where images of the colored restraint are not matched because the projected light is either absorbed to the extent that the images are not readily apparent, or the absorption by the restraint is such that the images are still apparent and the color of the restraint enables the images to be distinguished from the images of the patient and therefore not matched by the 3D position determination module 78.

In other embodiments, the patient restraint might have a distinguishable pattern to further aid or enable distinction between images of the patient and the patient restraint and the prevention of matching.

In an alternative embodiment, rather than utilizing the color of a restraint to prevent a model of the surface of the restraint being generated, the monitoring system could generate a model in a conventional way and instead utilize the color of the restraint to identify portions of a model which correspond to the surface of a patient and only utilize those portions of a model to monitor the position of a patient.

Thus for example in such a system, an additional color camera might be included in the stereoscopic camera system 10 used to monitor a patient. In such a system when the model generation module 80 had generated a model based on matches identified by a 3D position determination module 78, image data captured by the additional color camera could then be utilized to texture render the generated model. The texture rendered model could then be further processed by removing portions of the model which correspond to the color of the restraint so that the remaining portion of the model corresponded to a portion of the surface of the patient being monitored and this model could then be utilized to position the patient for treatment.

It will be understood the above described embodiments enable positioning of the patient with greater accuracy by generating a model of the patient without matching images of the patient restraint. This is achieved in alternative ways, either by physically preventing the patient restraint from being imaged by making it from a color that substantially absorbs the projected light, or using a distinguishably colored patient restraint and processing the images of the portion of the patient being monitored such that the images of the patient restraint are not matched or by texture rendering the portion of the patient being monitored using image data from an additional camera and removing the portions of model corresponding in color to the color of a restraint prior to utilizing the model to position a patient.

The invention claimed is:

1. A patient monitoring system comprising:
   a projector operable to project light onto a patient undergoing treatment;
   a patient restraint operable to restrain the patient relative to a treatment apparatus;
   a camera operable to obtain images of the patient and the patient restraint; and
   a model generation module operable to process images obtained by the camera to generate a model of the surface of a portion of a patient appearing in the images, wherein
      at least a portion of the patient restraint is colored and the model generation module is inhibited from generating a model of the colored portion of the patient restraint, and
      the colored portion of the patient restraint is arranged to absorb a substantial proportion of the projected light projected by the projector so that said projected light is not readily apparent in the portion of the images corresponding to the restraint, and
      the patient restraint comprises a head mask, the head mask including a frame and a sheet extending across the frame wherein an aperture is provided in the sheet, the arrangement of the aperture being such that when the sheet is deformed upon placement on a patient's head the aperture is such to leave at least part of the patient's face substantially free of the sheet.

2. The patient monitoring system of claim 1 wherein the model generation module is arranged to process images obtained by the camera to identify portions of images corresponding the colored portion of a patient restraint and only to attempt to identify corresponding portions of images outside the identified areas of the images.

3. The patient monitoring system of claim 1 wherein the colored portion of the patient restraint is colored black.

4. The patient monitoring system of claim 1 wherein the colored portion of the patient restraint corresponds to a color which substantially absorbs the pattern of light projected onto the patient by the projector.

5. The patient monitoring system of claim 1 wherein the colored portion of the restraint comprises a thermoplastic.

6. The patient monitoring system of claim 1 wherein the colored portion of the restraint contains a dye coloring the restraint.

7. The patient monitoring system of claim 1 wherein surface of the colored portion of the restraint is painted onto the exterior of the restraint.

8. The patient monitoring system of claim 1 wherein surface of the restraint has low reflectivity.

9. The patient monitoring system of claim 1 wherein the model generation module is arranged to identify corresponding portions of images by matching representations of corresponding portions of the projected pattern of light and is inhibited from generating a model of the colored portion of the patient restraint where the pattern of light is substantially absorbed.

10. The patient monitoring systems of claim 9 wherein the model generation module is arranged to utilize identified corresponding portions of images to determine the three dimensional positions of points corresponding to surfaces appearing in the images, wherein the model generation system is arranged to generate a model of a surface where identified points are separated from each other by no more than a threshold amount.

11. The patient monitoring system of claim 1 wherein the structure of the restraint is such that so that holes and perforations in the restraint appearing in images of the restraint obtained by the camera are of a different size to portions of a pattern of light projected onto the restraint utilized by the model generation module to identify corresponding portions of images.

12. The patient monitoring system of claim 1 wherein the projector is operable to project a pseudo-random pattern of light onto the surface of a patient being monitored.

13. A patient monitoring system comprising:
    a patient restraint operable to restrain the patient relative to a treatment apparatus, wherein at least a portion of the patient restraint is colored;
    a camera system operable to obtain first and second images of a portion of the patient being monitored; and
    a model generation module operable to process the first images obtained by the camera to generate a model of the surface of a portion of a patient appearing in the images and to process the second images to texture render the generated model of the portion of the patient, wherein
       the patient monitoring system is configured to monitor the position of a patient on the basis of the portion of the generated model which is not texture rendered a color corresponding to the color of the patient restraint, and
       the colored portion of the patient restraint is arranged to absorb a substantial proportion of projected light projected thereon so that a projected pattern is not readily apparent in the portion of the images corresponding to the restraint.

14. The patient monitoring system of claim 13 wherein the patient monitoring system is operable to compare the portion of the generated model which is not texture rendered a color corresponding to the color of the patient restraint with a stored model of the surface of a patient and to generate positioning instructions to match the portion for the generated model with the stored model.

15. The patient monitoring system of claim 13 wherein the colored portion of the patient restraint is patterned and the patient monitoring system is configured to identify portions of a generated model texture rendered with the pattern corresponding to the pattern appearing on the colored portion of the patient restraint.

16. The patient monitoring system of claim 13 wherein the colored portion of the patient restraint is a border around an aperture in the restraint and the patient monitoring system is configured to monitor the position of a patient on the basis of the portion of the generated model which is contained within the section of a model texture rendered a color corresponding to the colored border.

17. A blank for a head restraint comprising:
   a rigid frame; and
   a perforated sheet made of a material capable of being deformed over a patient's head, the perforated sheet extending across the frame, wherein
   an aperture is provided in the perforated sheet, the arrangement of the aperture being such that when the perforated sheet is deformed upon placement on a patient's head the aperture leaves a patient's face substantially free of the perforated sheet, and
   at least a portion of the perforated sheet is colored, such that the colored portion of the perforated sheet absorbs a substantial proportion of light projected thereon.

* * * * *